(12) United States Patent
Schumann et al.

(10) Patent No.: US 9,274,050 B2
(45) Date of Patent: Mar. 1, 2016

(54) PROCESS INTERFACE OF A PROCESS GAS ANALYZER OPERATING BY THE TRANSMITTED LIGHT METHOD

(71) Applicant: Siemens Aktiengesellschaft, Munich (DE)

(72) Inventors: Christian Schumann, Karlsruhe (DE); Yoann Stegle, Strassbourg (FR)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/325,480

(22) Filed: Jul. 8, 2014

(65) Prior Publication Data

US 2015/0077754 A1 Mar. 19, 2015

(30) Foreign Application Priority Data

Jul. 12, 2013 (DE) .......................... 10 2013 213 730

(51) Int. Cl.
*G01N 21/00* (2006.01)
*G01N 21/53* (2006.01)
*G01N 21/15* (2006.01)
*G01N 33/00* (2006.01)

(52) U.S. Cl.
CPC .............. *G01N 21/534* (2013.01); *G01N 21/15* (2013.01); *G01N 33/007* (2013.01); *G01N 2021/151* (2013.01); *G01N 2201/0612* (2013.01)

(58) Field of Classification Search
CPC ............ G01N 2021/151; G01N 21/15; G01N 21/534; G01N 2201/0612; G01N 33/007
See application file for complete search history.

(56) References Cited

U.S. PATENT DOCUMENTS

| 2010/0032264 A1* | 2/2010 | Pottmann ..................... 198/657 |
| 2010/0073679 A1 | 3/2010 | Larking et al. |
| 2011/0229307 A1* | 9/2011 | Lemieux et al. ............. 415/118 |

FOREIGN PATENT DOCUMENTS

| DE | 1993225 U | 9/1968 |
| DE | 102004018534 | 10/2006 |
| EP | 2169385 | 3/2010 |
| EP | 2428793 | 3/2012 |

* cited by examiner

*Primary Examiner* — Kara E Geisel
*Assistant Examiner* — Shawn Decenzo
(74) *Attorney, Agent, or Firm* — Cozen O'Connor

(57) ABSTRACT

A process interface of a process gas analyzer operating by a transmitted light method includes a purging tube, which extends between an optoelectronic element and an interior of a plant part carrying a process gas, wherein the purging tube is closed off, at its end opposite from the optoelectronic element by a window, in the vicinity of which a purging gas feed enters the purging tube, where an annular part is arranged in the interior of the purging tube opposite the entrance of the purging gas feed and is coaxial in relation to the purging tube, and the part has a convex outer side, the vertex line of which divides the entrance of the purging gas feed into a smaller region, open toward the window, and a larger region, open toward the interior of the plant part.

7 Claims, 1 Drawing Sheet ated to or separating from the window, the mode of flow in the region of the window is decisive for the effect of the purging gas. As a result of the flow of the purging gas around the annular part, the purging gas is calmed in particular in the region of the smaller inflow cross section between the annular part and the window, so that turbulences that disturb the measurement are avoided.

PROCESS INTERFACE OF A PROCESS GAS ANALYZER OPERATING BY THE TRANSMITTED LIGHT METHOD

BACKGROUND OF THE INVENTION

1. Field of the Invention

The invention relates to a process interface of a process gas analyzer operating by a transmitted light method, comprising a measuring head, which contains an optoelectronic element emitting or receiving light and is mounted on a process flange of a plant part containing or carrying a gas to be analyzed, a purging tube, which extends through the process flange between the optoelectronic element and the interior of the plant part, a window, closing off the purging tube at the end opposite from the optoelectronic element and separating the optoelectronic element from the interior of the plant part, a purging gas feed, entering the purging tube in a region close to the window, and an annular part, arranged in the interior of the purging tube opposite the entrance of the purging gas feed and coaxial in relation to the purging tube.

2. Description of the Related Art

EP 2 428 793 A1 discloses a conventional process interface.

In the case of gas analyzers operating by a transmitted light method, the light of a light source is passed through the gas to be analyzed and subsequently detected. In the case of a laser spectrometer, for example, the light is generated wavelength-selectively and is detected in a broadband range. As a difference from this, in the case of a non-dispersive infrared (NDIR) gas analyzer, for example, the light is generated in a broadband range and is detected wavelength-selectively. In the case of in-situ process gas analyzers, the light source and the detector are accommodated in different measuring heads, which are mounted on process flanges on diametrically opposite sides of a plant part containing or carrying the process gas to be measured (for example, an exhaust gas line, or vessel, flue). In order that the light source and the detector do not come into contact with the process gas, which is often aggressive, hot and contains dust, they are arranged behind windows. The window closes off one end of a purging tube, which at its other, open end enters the gas-carrying plant part and is flushed with a purging gas. The purging gas is chosen such that its spectral absorption lines lie outside the absorption lines of the process gas that are used for the measurement. The purging gas leaves from the open ends of the opposing purging tubes, so that the length of the measuring path for the absorption measurement of the process gas is determined by the distance between the open ends of the two purging tubes.

The greater the throughflow of purging gas, the more effectively it succeeds in keeping the windows free from contaminants from the process gas. However, a high consumption of purging gas entails correspondingly high costs and influences the measurement on account of the great quantities of purging gas that get into the measuring path between the opposing purging tubes.

The conventional process interface disclosed in the aforementioned EP 2 428 793 A1 has a purging gas feeding unit with a tubular flange entered by a purging gas feed. Pushed into the flange is a purging ring, which contains a system of interconnected grooves, in order to distribute the purging gas uniformly around the circumference, and finally conduct it via bores into the interior space of the tube. The bores are aligned such that they conduct the respective stream of gas away from the window to be purged. This is intended to ensure a homogeneous, virtually swirl-free inflow, so that the required quantity of purging gas can be reduced. Since the window is not flushed directly, when steam is used as the purging gas it may condense on the window.

DE 1 993 225 U describes a purging air attachment for the protection of optical surfaces, in the case of which an annular part arranged in the interior of the purging tube opposite the entrance of the purging gas feed and at a distance from the window forms between itself and the purging tube an annular gap that is open in the direction of the window and closed in the direction of the interior of the plant part. The purging gas is conducted completely to the window and deflected there, so that the stream of purging gas is subsequently in a swirled state. Turbulences disturb the measurement, in particular the measurement with a laser, and require a higher consumption of purging gas to achieve the same purging effect in comparison with an undisturbed homogeneous purging gas flow.

It is known from DE 10 2004 018 534 B4 to conduct the purging gas into the purging tube through a porous wall. Here, too, turbulences of the purging gas flow through the purging tube occur.

A process interface with a long purging tube is likewise known from EP 2 169 385 A1.

SUMMARY OF THE INVENTION

It is therefore an object of the invention to keep a window free from contaminants from a process gas and, if steam is used as the purging gas, prevent condensation thereof on the window, without a high consumption of purging gas being required, and so that the structural complexity involved in the purging is as low as possible.

These and other objects and advantages are achieved in accordance with the invention by providing a process interface in which the annular part has a convex outer side, the vertex line of which divides the entrance of the purging gas feed into a smaller region, open toward the window, and a larger region, open toward the interior of the plant part. The window is subjected to the flow of a smaller proportion of the quantity of purging gas through the smaller region, while at the same time the greater proportion of the quantity of purging gas is conducted into the purging tube through the larger region. The ratio of the proportions of the quantity of purging gas introduced in the direction of the window and directly into the purging tube can be established simply by the mounting position of the annular part in the purging gas tube. The proportion of the quantity of purging gas conducted toward the window, such as 10%, is just enough for the window to be flushed sufficiently, such as to avoid condensation but, on the other hand, the turbulences caused by the deflection of the flow at the window can be smoothed by the greater proportion of the quantity of purging gas, such as 90%, conducted into the purging gas tube in the direction of the plant part with the gas to be analyzed on the way to the plant part.

In order to hold the annular part in the interior of the purging tube, the annular part preferably contains along the vertex line a circumferential groove, in which a circlip is fitted. In addition, the purging tube may also contain within the interior a groove running through the entrance of the purging gas feed for receiving the circlip. As a result, mounting is made very much easier in comparison with previous solutions, in which gastight welding was necessary. The circlip is a standard part and as such can be obtained easily and inexpensively. The circlip itself contributes to the formation of the convex outer side of the annular part. As a result, it is preferably fitted such that its opening lies away from the entrance of the purging gas feed.

Apart from the quantitative proportions of the purging gas conducted into the purging gas tube, either toward the window or in the direction of the plant part with the gas to be analyzed, the respective angles at which the purging gas is introduced into the purging tube are also of importance for the purging result. These angles are dimensionally determined by the curvature of the convex outer side of the annular part on both sides of the vertex line. Preferably, the outer side of the annular part is formed on both sides of the vertex line as a lateral surface of a truncated cone, so that the purging gas flows into the purging tube approximately at the respective cone angle. The entrance of the purging gas feed lies in the vicinity of the window. As a result, a steeper angle is chosen for the flushing of the window than for the greater proportion of the flushing gas that is conducted into the purging tube in the direction of the gas to be analyzed. This greater proportion of purging gas preferably passes into the purging tube at a shallow angle, in order to ensure a homogeneous, virtually swirl-free inflow and further flow. For this purpose, it may also be provided that the purging tube tapers within a predetermined portion of the length from the entrance of the purging gas feed in the direction of the interior of the plant part to a width corresponding at least approximately to the inside diameter of the annular part. As a result, a flow cross section that remains the same is achieved for the proportion of purging gas coming from the window, so that no new turbulences can occur either. The tapering angle preferably corresponds approximately to the cone angle of the opposing outer contour of the annular part.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For further explanation of the invention, reference is made below to the drawing, in which.

DETAILED DESCRIPTION OF THE PREFERRED EMBODIMENTS

Figure 1:
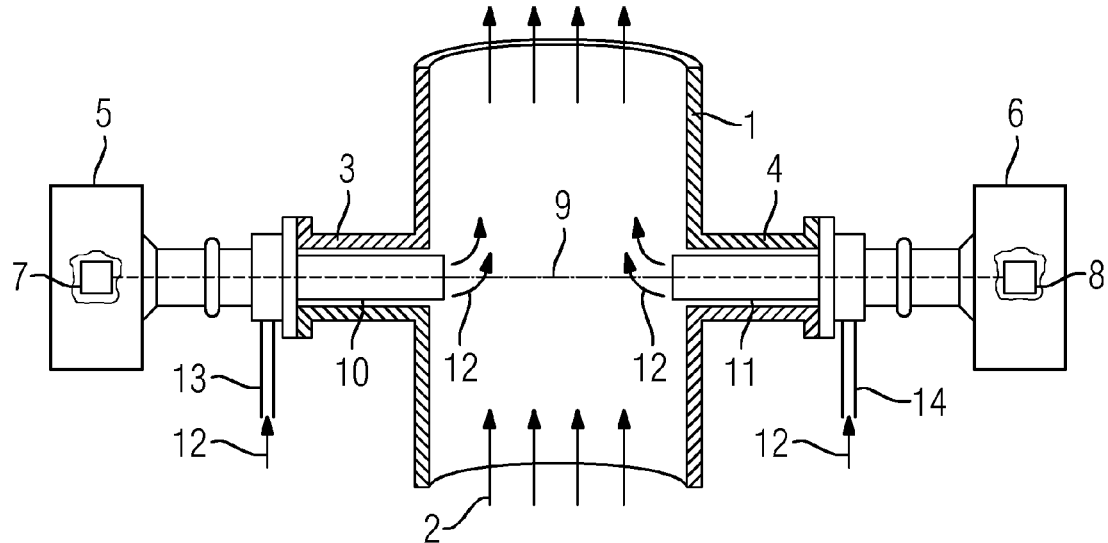
FIG. 1 shows an example of an in-situ process gas analyzer with two process interfaces.

FIG. 1 shows in a schematic representation a plant part 1, such as an exhaust gas duct, through which there flows a gas 2 to be analyzed. The plant part 1 has, at two diametrically opposed points, process flanges 3, 4, on which two measuring heads 5, 6 of substantially the same construction of a process gas analyzer are mounted. Both measuring heads 5, 6 respectively contain an optoelectronic element 7, 8, which in one case is a light source 7, such as a laser diode, and in the other case is a detector 8, such as a photodetector. The light 9 generated by the light source 7 is passed through the plant part 1 that carries the gas 2 within it and subsequently impinges on the detector 8. As explained in more detail below, the optoelectronic elements 7, 8 are separated from the interior of the plant part 1, and consequently from the gas 2, by a window (not shown), two purging tubes 10, 11, which are closed off at one end by the respective window and with their other, open end enter the interior of the plant part 1, being provided between the windows and the interior of the plant part 1. The purging tubes 10, 11, through which the light 9 passes, are flushed through by a purging gas 12. The purging gas 12 is introduced into the respective purging tube 10, 11 in the vicinity of the window through a purging gas feed 13, 14 and leaves the tube at its open end.

Figure 2:
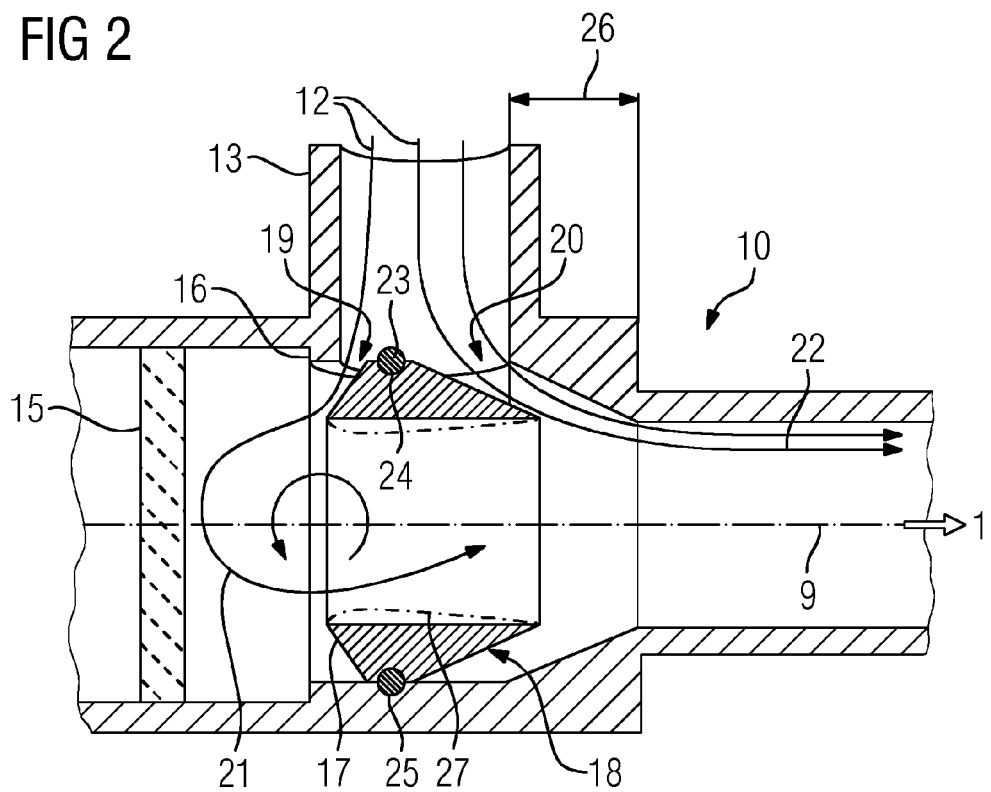
FIG. 2 shows an exemplary embodiment of one of the process interfaces.

FIG. 2 shows an example of the purging tube 10 closed off at one end by the window 15. At a distance from the window 15, the purging gas feed 13 enters the purging tube 10. Arranged in the interior of the purging tube 10, opposite the entrance 16 of the purging gas feed 13, is an annular part 17, which is coaxial in relation to the purging tube 10. The outer side 18 of the annular part 17 is formed as a convex lateral surface, the vertex line of which divides the entrance 16 of the purging gas feed 13 into a smaller region (opening gap) 19, open toward the window 15, and a larger region 20, open toward the interior of the plant part 1. The ratio of the two regions 19 and 20 is, for example, 1:9. In the case of the example shown here, the profile of the annular part 17 is triangular or trapezoidal, i.e., the outer side 18 of the annular part 17 is formed on both sides of the vertex line respectively as the lateral surface of a truncated cone with a different cone angle. The purging gas 12 introduced into the purging tube 10 is divided by the annular part 17 into a smaller proportion 21 in the direction of the window 15 and a greater proportion 22 in the direction of the interior of the plant part 1, the smaller proportion 21 flowing at a comparatively steep angle in relation to the window 15, while the greater proportion 22 passes into the purging tube 10 at a very shallow angle, free from turbulence, and flows further in the direction of the interior of the plant part 1.

The annular part 17 is held in the interior of the purging tube by means of a circlip 23, which lies in a circumferential groove 24, running along the vertex line, of the annular part 17, and a further groove 25, running through the entrance 16 of the purging gas feed 13, of the purging tube 10. The circlip 23 is oriented such that its opening lies in a region away from the entrance 16 of the purging gas feed 13.

In the case of the exemplary embodiment shown, the purging tube 10 tapers within a portion of the length 26 from the entrance 16 of the purging gas feed 13 in the direction of the interior of the plant part 1 to a width corresponding to the inside diameter of the annular part 17. The tapering angle corresponds approximately to the cone angle of the opposing outer contour 18 of the annular part 17. Additionally or alternatively, the inner side 27 of the annular part 17 may be convexly curved, as indicated by dash-dotted lines, such that the cross section of the annular part 17 has a wing profile with the front edge toward the window 15.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A process interface of a process gas analyzer operating by a transmitted light method, comprising:
   a measuring head including a optoelectronic element emitting or receiving light, the measuring head being mountable on a process flange of a plant part containing or carrying a gas to be analyzed,
   a purging tube extending through the process flange between the optoelectronic element and an interior of the plant part;
   a window closing off the purging tube at an end opposite from the optoelectronic element and separating the optoelectronic element from the interior of the plant part;
   a purging gas feed entering the purging tube in a region close to the window; and
   an annular part arranged in the interior of the purging tube opposite an entrance of the purging gas feed and coaxial in relation to the purging tube, the annular part including a convex outer side, a vertex line of which divides the purging gas feed upon entry to the purging tube into a smaller region to divert a smaller portion of the purging gas, open toward the window, and a larger region to divert a greater portion of the purging gas, open toward the interior of the plant part.

2. The process interface as claimed in claim 1, wherein the annular part contains, along the vertex line, a circumferential groove, into which a circlip holding the annular part in the interior of the purging tube is fitted.

3. The process interface as claimed in claim 2, wherein the purging tube contains, in its interior, a groove extending through the entrance of the purging gas feed for receiving the circlip.

4. The process interface as claimed in claim 2, wherein an opening of the circlip is disposed in a region arranged away from the entrance of the purging gas feed.

5. The process interface as claimed in claim 3 wherein an opening of the circlip is disposed in a region arranged away from the entrance of the purging gas feed.

6. The process interface as claimed in claim 1 wherein the convex outer side of the annular part is formed on both sides of the vertex line as a lateral surface of a truncated cone.

7. The process interface as claimed in claim 1 wherein the purging tube tapers within a predetermined portion of a length from the entrance of the purging gas feed in a direction of the interior of the plant part to a width corresponding at least approximately to an inside diameter of the annular part.

\* \* \* \* \*